US011154581B2

(12) United States Patent
Yang

(10) Patent No.: US 11,154,581 B2
(45) Date of Patent: Oct. 26, 2021

(54) METHOD FOR IMPROVEMENT OF STIFF NECK AND SHOULDERS

(71) Applicant: TOKIWA PHYTOCHEMICAL CO., LTD., Sakura (JP)

(72) Inventor: Jinwei Yang, Sakura (JP)

(73) Assignee: TOKIWA PHYTOCHEMICAL CO., LTD., Sakura (JP)

( * ) Notice: Subject to any disclaimer, the term of this patent is extended or adjusted under 35 U.S.C. 154(b) by 0 days.

(21) Appl. No.: 16/740,843

(22) Filed: Jan. 13, 2020

(65) Prior Publication Data

US 2020/0147162 A1 May 14, 2020

Related U.S. Application Data

(62) Division of application No. 15/643,856, filed on Jul. 7, 2017, now abandoned.

(30) Foreign Application Priority Data

Mar. 15, 2017 (JP) .............................. JP2017-050667

(51) Int. Cl.
*A61K 36/45* (2006.01)
*A61K 31/352* (2006.01)

(52) U.S. Cl.
CPC ............ *A61K 36/45* (2013.01); *A61K 31/352* (2013.01); *A61K 2236/333* (2013.01); *A61K 2236/51* (2013.01)

(58) Field of Classification Search
None
See application file for complete search history.

(56) References Cited

U.S. PATENT DOCUMENTS

| 2009/0176718 | A1 | 7/2009 | Ribnicky et al. |
| 2009/0181901 | A1 | 7/2009 | Eidenberger |
| 2011/0217418 | A1* | 9/2011 | Eidenberger ........... A61K 36/45 426/72 |
| 2012/0277173 | A1 | 11/2012 | Eidenberger |
| 2013/0323843 | A1 | 12/2013 | Yoon et al. |
| 2015/0004142 | A1 | 1/2015 | Caldwell et al. |
| 2017/0281481 | A1 | 10/2017 | Pacchetti |
| 2018/0050071 | A1 | 2/2018 | Bizzini |

FOREIGN PATENT DOCUMENTS

| CN | 103860625 A | 6/2014 |
| JP | 2007 308396 | * 11/2007 |
| JP | 2016 183121 | * 10/2016 |
| JP | 2016-183121 A | 10/2016 |
| JP | 2018-140956 A | 9/2018 |

OTHER PUBLICATIONS

Bilberon(TM) info sheet from www.bilberon.com/english/#top (Year: 0).*
Park, H. et al. Antiapoptotic Effects of Anthocyanins on Rotator Cuff Tenofibroblasts. J of Orthopaedic Research 28(9)1162-1169, 2010. (Year: 2010).*
Kono, K. et al. Effect of Multiple Dietary Supplement Containing Lutein, Astaxanthin, Cyanidin-3-Glucoside . . . Immunology, Endocrine & Metabolic Agents in Medicinal Chemistry 14(2)114-125, 2014. (Year: 2014).*
Kawabata, F. et al. Effects of Dietary Supplementation with a Combination of Fish Oil, Bilberry Extract, and Lutein on Subjective Symptoms of Asthenopia in Humans. Biomedical Research 32(6)387-393, 2011. (Year: 2011).*
Kono, K. et al. Effect of Multiple Dietary Supplement Containing Lutein, Astaxanthin, Cyanidin-3-Glucoside, and DHA on Accomodative Ability. Immunology, Endocrine & Metabolic Agents in Medicinal Chemistry 14(2)114-125, 2014. (Year: 2014).*
The Effect of Air-Drying, Freeze-Drying and Storage on the Quality and Antioxidant Activity of Some Selected Berries, by M. Michalczyk et al, Journal of Food Processing and Preservation, vol. 33, 11-21, 2009 (English Abstract Only, 2 pages).
Extraction of phenolic compounds and anthocyanins from blueberry (*Vaccinium myrtillus* L.) residues using supercritical CO2 and pressurized liquids, by J. Paes et al, Journal of Supercritical Fluids, vol. 95, 8-16, 2014 (9 pages).
Effects of dietary supplementation with a combination of fish oil, bilberry extract, and lutein on subjective symptoms of asthenopia in humans, by F. Kawabata et al, Biomedical Research, vol. 32 (6), 387-393, 2011 (7 pages).
Effect of a Bilberry Extract (BILBERON)-containing Diet on the Improvement of Eye Fatigue-related Symptoms (II), by T. Liang et al, Japanese Pharmacology and Therapeutics vol. 45, No. 9, 1523-1534, 2017 (12 pages).
The effect of a natural, standardized bilberry extract (Mirtoselect) in dry eye: a randomized, double blinded, placebo-controlled trial, by A. Riva et al, European Review for Medical and Pharmacological Sciences, vol. 21, 2518-2525, 2017 (8 pages).
Clinical evidence on potential health benefits of berries, by B. Yang et al, Current Opinion in Food Science, vol. 2, 36-42, 2015 (English Abstract only, 2 pages).
Indena Website www.us.indena.com Mirtoselect.info 1-6 no date given (Year 2018) (6 pages).
Non-Carotenoid nutraceuticals for treatment of eye diseases, by A. Newport et al, Agro Food Industry Hi-Tech, vol. 19(2), 47-49, 2008 (4 pages).

(Continued)

Primary Examiner — Ralph J Gitomer
(74) Attorney, Agent, or Firm — Flynn Thiel, P.C.

(57) ABSTRACT

A composition and method for the prevention and/or improvement of dry eye syndrome, dryness of eye and/or stiff neck and shoulder, which contains bilberry fruit extract and is effective with less intake are provided. As one aspect of the present invention, the composition for the prevention or improvement of dry eye syndrome or dryness of eye contains a freeze-dried bilberry fruit extract. As another aspect of the present invention, the composition for the prevention or improvement of stiff neck and shoulder contains a freeze-dried bilberry fruit extract. As another aspect of the present invention, a composition for the prevention or improvement of dry eye syndrome, dryness of eye, and stiff neck and shoulder, contains a freeze-dried bilberry fruit extract. As another aspect of the present invention, a method using a bilberry fruit extract for the improvement of stiff neck and shoulder is provided.

1 Claim, No Drawings

(56) References Cited

OTHER PUBLICATIONS

Dry Eyes and Video Display Terminals, by K. Tsubota et al, The New England Journal of Medicine, vol. 328, p. 584, 1993 (1 page).

Blinking and Tear Break-Up During Four Visual Tasks, by N. Himebaugh et al, Optometry and Vision Science, vol. 86, No. 2, pp. E106-E114, 2009 (9 pages).

Effects of blue light on the circadian system and eye physiology, by G. Tosini et al, Molecular Vision, vol. 22, pp. 61-72, 2016 (12 pages).

Damage of photoreceptor-derived cells in culture induced by light emitting diode-derived blue light, by Y. Kuse et al, Scientific Reports, vol. 4, 5223, pp. 1-12, 2014 (13 pages).

* cited by examiner

METHOD FOR IMPROVEMENT OF STIFF NECK AND SHOULDERS

This application is a divisional of prior U.S. application Ser. No. 15/643,856, filed Jul. 7, 2017, which is hereby incorporated by reference in its entirety.

TECHNICAL FIELD

The present invention relates to a composition, which includes bilberry extract, for the prevention and/or improvement of at least one of dry eye syndrome, dryness of the eye, and stiff neck and shoulder.

RELATED ART

Bilberry (*Vaccinium myrtillus*) is a small fruit tree of *Vaccinium* of Ericaceae. It is a wild species and mainly grows naturally in Northern Europe.

Bilberry fruits have been popular as juices and jams for a long time. Especially, in Europe, functions of bilberry fruits are actively studied. Bilberry includes anthocyanin, which is a polyphenol. There are many reports that anthocyanin has many bioactivities such as an antiangiogenic effect, antibacterial effect, antidiabetic effect, antitumor effect, and anti-obesity effect.

Incidentally, in recent years, working times with Visual Display Terminals (VDT) have become longer by the development of information technology.

Here, "VDT work" means that the work in which VDT, such as a display and a key board, are used.

In VDT work, it is reported that the number of times of eye blinking becomes decreased (see Non-patent literature 1) and dryness of eye is induced by incomplete blinking (see Non-patent literature 2).

Especially, many light sources used in VDT work are light-emitting diodes (LED). It is reported that generation of active oxygen occurs by the overexposure of the blue-light which is emitted from the LED (Non-patent literature 3,4).

Then, it is thought that the active oxygen is the origin of asthenopia, dry eye syndrome, and/or dryness of eye.

Non-Patent Literature

Non-patent literature 1 Tsubota K, Nakamori K. "Dry eyes and video display terminals.", N Engl J Med. 1993; 328: 584.
Non-patent literature 2 Himebaugh N, Begley C, Bradley A, Wilkinson J. "Blinking and tear break-up during four visual tasks.", Optom Vis Sci. 2009; 86: E106-14.
Non-patent literature 3 Tosini G, Ferguson I, Tsubota K. "Effects of blue light on the circadian system and eye physiology." Molecular Vision. 2016; 22:61-72.
Non-patent literature 4 Kuse Y, Ogawa K, Tsuruma K, Shimazawa M, Hara H., "Damage of photoreceptor-derived cells in culture induced by light emitting diode-derived blue light.", Sci Rep., 2014; 4: 5223.

DESCRIPTION OF THE INVENTION

Problems to be Solved by the Invention

Incidentally, it is thought that anthocyanin derived from blueberry may be effective for asthenopia.

However, the correlation between the extract of bilberry-fruits and the efficacy of dry eye syndrome and/or dryness of eyes is not clear.

Further, in an aspect of economy, it is desirable that the effects can be obtained with less intake.

The less intake of anthocyanin brings a reduction in the cost of commodities, and it is possible to provide commodities with a lower cost for consumers.

Then, in consideration of the above-mentioned problem, the object of the present invention is to provide a composition for the prevention and/or improvement of dry eye syndrome, dryness of eye and/or stiffness, which contains bilberry fruit extract and is effective with less intake.

Solution to the Problems

From research on bilberry fruit extract, the inventors found that freeze-dried bilberry fruit extract can improve dry eye syndrome, dryness of eye and/or stiff neck and shoulder.

Thus, a composition of one aspect of the present invention is for the prevention and/or improvement of dry eye syndrome and/or dryness of eye, and the composition contains freeze-dried bilberry fruit extract.

Further, a composition of another aspect of the present invention is for the prevention and/or improvement of stiff neck and shoulder, and the composition contains freeze-dried bilberry fruit extract.

Thus, a composition of one aspect of the present invention is for the prevention and/or improvement of dry eye syndrome, dryness of eye, and/or stiff neck and shoulder, and the composition contains freeze-dried bilberry fruit extract.

Further, a method for producing a composition for the prevention and/or improvement of dry eye syndrome, dryness of eye and/or stiff neck and shoulder, which is another aspect of the present invention, comprises a step of obtaining bilberry extract by using water-containing ethanol, and a step of freeze-drying the bilberry extract.

Effects of the Invention

Thus, by the present invention, it is possible to provide a composition for the prevention and/or improvement of dry eye syndrome, dryness of eye and/or stiff neck and shoulder, which includes bilberry fruit extract and is effective with less intake.

BEST MODE FOR CARRYING OUT THE PRESENT INVENTION

Hereafter, embodiments of the present invention will be described. However, the present invention can be carried out with many other embodiments and is not limited to the embodiments described below.

A composition of one aspect of the embodiment of the present invention (hereafter "the composition") comprises bilberry fruit extract which is freeze-dried.

In the composition, "bilberry-fruit extract" is the extract that is extracted from bilberry (botanical name: *Vaccinium mytrillus* L., English name: Bilberry).

It is desirable that a raw material for the bilberry fruit extract is such as a plant itself, a dried-fruit, a ground product, a puree, or a raw fruit juice.

Further, the bilberry fruit extract can be obtained by solvent extraction from a raw material itself or a processed material which is properly processed.

The extract includes a filtrate which is obtained by filtering the extract, a concentrated material which is obtained from the extract by removing a solvent and concentrated, a purified product which is obtained by removing impurities from the extract, and a solid material which is obtained from those liquids by evaporating the liquid component.

A method for concentrating the extract is adoptable such as evaporative concentration and membrane concentration, but it is not limited to them.

Further, the method for purifying can be carried out using at least one of a synthetic adsorption resin, an activated carbon, an ion-exchange resin, a gel filter material such as sephadex and bio-gel, chromatography, and recrystallization.

Further, here, it is desirable that the solvent which is used in solvent extraction comprises at least one of water, alcohol and glycerin. Further, a water-containing alcohol is more desirable. But it is not limited to them.

Here, it is desirable that the alcohol comprises at least one of methanol, ethanol, propanol, isopropanol and butanol, and it is more desirable that the alcohol comprises ethanol. But it is not limited to them, too.

In the case of water-containing ethanol, it is desirable that ethanol is included in an amount of 20 wt % or more and 99 wt % or less. Moreover, 40 wt % or more and 90 wt % or less is more desirable, and 60 wt % or more and 90 wt % or less is the most desirable.

Further, the bilberry fruit extract of the composition is a freeze-dried composition.

In this embodiment, the method of freeze-drying comprises a freezing step in which the bilberry fruit extract is frozen rapidly at a low temperature, and a drying step in which the frozen extract is dried with a pressure reduction. But it is not limited to them.

In the drying step, as a realistic range, it is desirable that the freezing temperature is −10 degree Celsius or less and −50 degree Celsius or more. But, it is not limited to it as long as it is possible to freeze the bilberry fruit extract.

Further, in the step, it is desirable that the freezing rate is rapid for maintaining a uniform dispersion state of the bilberry fruit extract. Specifically, it is desirable that the freezing rate is −5 degree Celsius per hour or more and −20 degree Celsius per hour or less.

Further, in this case, it is desirable that the concentration of the solid content of the bilberry fruit extract is 5 wt % or more and 50 wt % or less, 10 wt % or more and 40 wt % or less is more desirable, and 30 wt % is especially desirable. But it is not limited to them as long as it is possible to freeze the extract.

Further, a low concentration is desirable because it is easy to obtain smaller particles.

Further, in the step of drying with a pressure reduction, it is desirable that the step comprises a step of reducing the pressure at room temperature, and a step of heat-drying at the reduced pressure.

Here, it is desirable that the length of time of the pressure reduction is 10 hours or more and 50 hours or less. But it is not limited to it as long as it is possible to dry the extract.

Further, it is desirable that the temperature of heat-drying is 20 degree Celsius or more and 50 degree Celsius or less, and 40 degree Celsius or less is more desirable. But it is not limited to it. Within the above-mentioned range, it is possible to obtain extract particles efficiently with a reduction in the decomposition of the active ingredient.

Further, it is desirable that the time of heating is 1 hour or more and 10 hours or less.

In this embodiment, since the composition is produced by freeze-drying the bilberry fruit extract, it is possible to obtain the fruit extract with the maintaining of the active ingredient (anthocyanin) stably.

Further, since it is possible to obtain smaller particles by freeze-drying, it is possible that the extraction rate of the active ingredient is high, and the prevention and/or improvement of dry eye syndrome (dryness of eye) with a less amount is realized.

On the other hand, in spray-drying, as a drying step is carried out with heating, the active ingredient of the bilberry fruit extract decomposes at high temperature and the effect of the extract will be less.

Further, it is obvious that the color of the bilberry fruit extract which is obtained by freeze-drying is markedly different from the extract which is obtained by other ways of drying.

It is thought that, by freeze-drying, the particle size is smaller than that of other ways such as spray-drying, and the extract will be more effective.

Specifically, it is possible to realize that, in particle size distribution, the 10% particle size is 4 µm or less. In some cases, it is possible to realize 3 µm or less.

The particle size distribution is measurable by a particle counter.

In the composition, it is considered that the active ingredient is anthocyanin which is extracted from bilberry.

It is desirable that the anthocyanin extracted from bilberry is contained in an amount of 30 wt % or more and 50 wt % or less in the composition. It is more desirable that the anthocyanin is contained in an amount of 35 wt % or more and 50 wt % or less.

Further, in addition to the above-identified freeze-dried bilberry fruit extract, it is possible that the composition can include an excipient, coloring material, sweetening agent, and suspending agent.

As an excipient, dextrin is desirable, but it is not limited thereto.

Further, it is desirable that the form of the composition is such as a food, medicine or cosmetic.

Especially, in the case of a food, a functional food or health food is desirable.

Moreover, in the case of a food, it is desirable the state is a solid matter or drink.

Further, in the case that the composition is a food, the form can be dessert such as a drink, a candy, a jelly, or a gummy candy.

In the case that the composition is health food or functional food, the form can be such as a tablet, a hard capsule, a soft capsule, a granule or a drink.

Further, in the case that the composition is a medicine, the form can be such as a tablet, a capsule, a pill, a liquid, or an emulsion.

It is preferable that the method of medication is oral administration, but it is not limited to it.

Further, it is possible to add various support medium, such as an excipient, a coloring agent, a sweetening agent, and a suspending agent, within the pharmaceutically acceptable range.

Further, the content of bilberry-fruit extract in the composition is adjustable for an estimated amount of intake, but, in case of a tablet, a capsule or a pill, it is desirable that the content is 10 wt % or more and 95 wt % or less, and it is more desirable that it is 15 wt % or more.

For obtaining the effect of the prevention and/or improvement of dry eye syndrome or dryness of eye, it is good that the amount of intake of bilberry fruit extract is 500 mg per day or less, with 100 mg per day or more and 400 mg per day being desirable, 300 mg or less being more desirable, and 160 mg per day being the most desirable. If the intake is 120 mg per day or more, it is possible to certainly obtain the effect.

Incidentally, the composition has an effect of the prevention and/or improvement of dry eye syndrome, dryness of eye and/or stiff neck and shoulder.

The range which the effect can be obtained will be clear by the below-described examples.

Thus, by the present invention, it is possible to provide a composition for the prevention and/or improvement of dry eye syndrome, dryness of eye and/or stiff neck and shoulder, which contains bilberry fruit extract and is effective with less intake.

EXAMPLES

The effect of the invention was confirmed by producing the composition of the above-mentioned embodiment actually. Hereafter, the examples will be specifically described.

(1) Producing Bilberry Fruit Extract

First, frozen fruit of bilberry (*Vaccinium myrtillus*) was crushed, and water-containing ethanol was added to the crushed bilberry. Then, after extraction, a filtrate was obtained.

After concentrating the filtrate and refining which used a resin, a purified liquid was obtained.

After concentrating the purified liquid, a bilberry fruit extract was obtained.

Then, the concentration which included the bilberry fruit extract (solid content) 30 wt % was frozen at −30 degree Celsius for 5 hours.

The frozen extract was put in a freeze-drier, and it was dried with decompression to 100 Pa at room temperature.

Additionally, the temperature was increased up to 30 degree Celsius, and the material was dried at 100 Pa which was same as above.

By high performance liquid chromatography, it was found that the amount of anthocyanin in the extract was 36 wt % per the total weight of bilberry fruit extract.

(2) Clinical Test

The test subjects were healthy (but had eyestrain) Japanese adults who daily played TV games, use computers or smartphones, or do VDT work, for 4 hours or more, and feel eyestrain.

In the clinical test, test hard capsules, each of which included 40 mg of bilberry fruit extract (14.4 mg of anthocyanin extracted from bilberry was included), were used.

Further, placebo capsules were prepared by filling such as food additives into hard capsules so that the appearances were the same as the test hard capsules (test food).

Then, 22 Japanese adults were divided in two groups. One was an intervention group and the other was a placebo group.

The adults of the intervention group took the bilberry fruit extract 120 mg per day for 6 weeks or 160 mg per day for 6 weeks.

The adults of the placebo group took the placebo capsules for 6 weeks the same as that of the intervention group.

As a result of Schirmer's test, which measures the amount of lachrymal fluid, the sensation of dryness of eye dryness and stiff shoulder were evaluated, before taking the extract and after 6 weeks after taking it.

The evaluations of sensation were carried out before taking the extract and at the sixth week after taking it. Further, the evaluations were carried out before VDT load of portable game (60 minutes) and after the VDT load, respectively.

(3) Result of Schirmer's Test when the Amount of Intake was 120 mg Per Day

The length of the wet part of the test paper of the left eye of the intervention group was increased 80.2% (p=0.037) at the sixth week after taking the extract, and that of right eye was also increased 16.9% (p=0.10). The average was increased 44.5% (p=0.032).

Moreover, by a comparison between the groups, at the sixth week after taking the extract, the amount of lachrymal fluid of the right eye of the intervention group was significantly increased, compared to the placebo group (p=0.048).

Though a similar trend could not be found at the average of the right and left eyes, it was confirmed that the amount of lachrymal fluid of the intervention group was increased (p=0.07).

(4) Sensation when the Amount of Intake was 120 mg Per Day

In the intervention group, the score of the subjective symptom was significantly decreased in item of "I feel my eyes are dry (after VDT load test)" of a questionnaire at the sixth week after taking the extract (p=0.018).

(5) Schirmer's Test when the Amount of Intake was 160 mg Per Day

In the intervention group, the length of the wet part of the test paper was increased 11.3% in the left eye, 50.2% in the right eye, and 20.6 as the average.

On the other hand, in the placebo group, the length of the wet part of the test paper was decreased 52.2% in the left eye, 21.9% in the right eye, and 40.0% as the average, at the sixth week after taking the placebo capsules.

By a comparison between the two groups at the sixth week after taking the extract, the amount of lachrymal fluid of the right eye of the intervention group was significantly increased, compared to the placebo group (p=0.024).

Though a similar trend could not be found at the average of the right and left eyes, it was confirmed that the amount of lachrymal fluid of the intervention group was increased (p=0.071), compared to the placebo group.

(6) Sensation of Dryness of Eye when the Amount of Intake is 160 mg Per Day

The score of the subjective symptom of the intervention group was significantly decreased (p=0.044) in item of "I feel dryness of the eye (after VDT work)" of a questionnaire at the sixth week after taking the extracts.

(7) Effect of Improvement of Stiff Neck and Shoulder when the Amount of Intake is 120 mg Per Day The score of the subjective symptom of the intervention group was significantly decreased (placebo group: 4.5±1.8, interventional group: 3.4±1.0, p=0.09) in item of "I feel stiff neck and shoulder (after VDT test)" of a questionnaire at the 6th week after taking the extract.

(8) Effect of the Improvement of Stiff Neck and Shoulder when the Amount of Intake is 160 mg Per Day Further, the score after intake was significantly decreased in the item "I feel a stiff neck and shoulder (before VDT test)" of the questionnaire.

Further, the score of subjective symptom of the intervention group was significantly decreased (p=0.004) at the sixth week after taking the extract, compared to the placebo group.

Additionally, in item of "I feel a stiff neck and shoulder (after VDT load test)" of a questionnaire of the subjective symptom, the score of the intervention group was significantly decreased after taking the extract (p=0.038).

Moreover, the score of the intervention group was significantly decreased compared to the placebo group at the sixth week after taking the extract (p=0.029).

(Particle Size Distribution of Freeze-Dried Composition)

The particle size distribution of the freeze-dried composition was confirmed.

Here, the bilberry fruit extract was obtained in the same way as the above-identified (1), and the bilberry fruit extracts freeze-dried so that the concentration of the solid content was 10 wt % or 30 wt %, respectively.

As a result, it was found that the minimum particle diameter was 0.159 μm at 10 wt %, and 10% particle diameter (d10) was 3.29 μm. Thus, it was confirmed that the diameters were very small.

Further, at 30 wt %, the minimum particle diameter was 0.159 μm and 10% particle diameter (d10) was 2.76 μm. It was confirmed that the diameter was extremely small.

On the other hand, in the case of spray drying, the minimum diameter was 0.63 μm, the 10% particle diameter (d10) was 6.86 μm. the diameters were large.

This means that in the case of bilberry fruit extract, it is possible to obtain smaller particles without decomposition of the active ingredient by freeze-drying.

This also means that the extract can be taken in the body with a smaller particle diameter, and the transfer rate to eye will be high.

By the above test, it is confirmed that it is possible to obtain a composition for the prevention and/or improvement of dry eye syndrome, dryness of eye and/or stiff neck and shoulder, which contains a bilberry fruit extract and is effective with less intake.

Especially, as the transition rate of the anthocyanin of the above experiment derived from bilberry is high, it is possible to transfer anthocyanin to eyes effectively and obtain a high effect.

What is claimed is:

1. A method for treating stiff neck and shoulders comprising the steps of:
    administering to a subject a bilberry extract from 120 mg to 500mg per day, the bilberry extract containing anthocyanin in an amount of 30% to 50% by weight, and a D10 particle diameter size of the bilberry extract being 4 μm or less,
    said bilberry extract obtained by an extraction process using a first solvent that contains water, or ethanol, or a mixture of water and ethanol, and a freeze-drying process at a low temperature and a low pressure.

* * * * *